United States Patent [19]

Mount, II et al.

[11] Patent Number: 4,854,163

[45] Date of Patent: Aug. 8, 1989

[54] BELTLESS CORE CONVEYOR SYSTEM FOR WELLSITE ANALYSIS

[75] Inventors: Houston B. Mount, II; Michael L. Snoddy, both of Tulsa, Okla.

[73] Assignee: Amoco Corporation, Chicago, Ill.

[21] Appl. No.: 101,461

[22] Filed: Sep. 28, 1987

[51] Int. Cl.$^4$ .............................................. E21B 49/02
[52] U.S. Cl. .................................... 73/153; 250/359.1; 378/53; 198/750
[58] Field of Search ................. 73/153; 250/337, 255, 250/359.1, 358.1, 270; 378/53, 51; 198/750, 775, 768, 715

[56] References Cited

U.S. PATENT DOCUMENTS

| | | | |
|---|---|---|---|
| 2,669,344 | 2/1954 | Flint | 198/768 X |
| 2,859,349 | 11/1958 | Bradley et al. | 250/358.1 X |
| 3,212,630 | 10/1965 | Allen et al. | 198/768 |
| 3,373,440 | 3/1968 | Jenkins et al. | 346/139 R |
| 3,414,725 | 12/1968 | Evans | 378/51 |
| 3,666,092 | 5/1972 | Anderson | 198/750 X |
| 4,090,074 | 5/1978 | Watt et al. | 378/53 X |
| 4,278,882 | 7/1981 | Clayton et al. | 250/255 |
| 4,485,308 | 11/1984 | Rabatin | 250/271 X |
| 4,582,992 | 4/1986 | Atwell et al. | 250/359.1 |
| 4,641,242 | 2/1987 | Kimura | 250/337 X |

FOREIGN PATENT DOCUMENTS

| | | | |
|---|---|---|---|
| 0016784 | 2/1977 | Japan | 198/768 |
| 0818988 | 4/1981 | U.S.S.R. | 198/750 |
| 1039832 | 9/1983 | U.S.S.R. | 198/768 |
| 2066456 | 7/1981 | United Kingdom | 250/358.1 |

Primary Examiner—Eugene R. LaRoche
Assistant Examiner—Seung Ham

[57] ABSTRACT

A core trough is driven by drive means along a path adjacent analysis means for preliminary analysis of sectioned core taken during stratigraphic exploration.

23 Claims, 5 Drawing Sheets

BELTLESS CORE CONVEYOR SYSTEM FOR WELLSITE ANALYSIS

FIELD OF THE INVENTION

The invention relates to analysis of cores removed from well boreholes. In a particular aspect, the invention relates to such analysis specially adapted for handling large quantities of core as such core is being produced at the wellsite.

PRIOR ART

U.S. Pat. No. 3,373,440 describes customary practice in the drilling of some oil and gas wells. When the drilling bit approaches a formation which may contain oil or gas, a coring bit and core barrel are substituted for a drill bit and core samples are taken. The core samples can then be analyzed for such characteristics as lithology, porosity, permeability, oil and water saturation, and the like. Such analysis typically occurs in a commercial laboratory which provides such services to the industry. U.S. Pat. No. 3,373,440 particularly relates to a system for photographing cores and detecting radiation from cores.

SETTING OF THE INVENTION

More recently, it is proposed to drill stratigraphic exploration wells using special coring bits and core barrels and to take core along substantially the entire depth of penetration. The core is then analyzed for indicia of the presence of oil and gas.

Compared to the previous practice of coring only portions of a well, the practice of stratigraphic exploration requires thousands of feet of core to be produced from each well. The produced core must then be preliminarily analyzed at least sufficiently to show which portions of the core should be subjected to a more detailed analysis and to provide information in correlating data from the well with information obtained from other sources, for example, from logging, aeromagnetic surveys, seismic exploration, and the like. Photographs of the core, while useful, are not of themselves sufficient for this preliminary analysis in connection with stratigraphic exploration wells.

For example, the borehole after drilling and taking of core can be logged with a gamma ray detector measuring the natural radioactivity of the formation adjacent the borehole. Such logging in addition to providing data on natural radiation provides a rough correlation of depth to variations in natural radiation along the borehole. For purposes of identifying portions of the core for further analysis, however, and for correlating the results of other logging tools to the subterranean locations, such rough correlations do not suffice. For more precise correlations between core and subterranean formations adjacent the borehole, the core also must be scanned for natural radioactivity. Then, the gamma ray record for the core can be correlated to the gamma ray record for the formation and to other measurements made on the core. Thus, measurements such as porisity, permeability, and the like made on the core can be precisely correlated with the formations adjacent the borehole.

Other analytical scanning of the core is also useful. Infrared scanning of the core can provide mineralogical information directly, thus, providing indications of clay types, quartz, limestone, dolomite, and the like. Also, magnetic susceptibility measurements made on the core can provide a basis for correlating a well with aeromagnetic surveys of the region where the well is being drilled. Also, measurements of seismic travel time on core specimens can provide a basis for correlating core with seismic surveys in the region.

Such preliminary analysis of substantially all of the core taken from the wellbore if carried out in the usual way would require transportation of the core to a core analysis facility where it would be first analyzed for one set of characteristic, then for another, and the like. Then, core would be selected for further analysis, and the remaining core would be disposed of or sent to core storage facilities.

By contrast, if the core can be preliminarily analyzed at the drilling site, only portions selected for further analysis need be transported to a core analysis facility. The remaining core can be disposed of or directly transported to a core storage facility. Further, it is desirable to handle the core only once for a series of analyses. The savings in time and expense of handling are apparent. The preliminary core analysis system should also be capable of making multiple measurements on up to 20 ft or more of core per hour so that the preliminary core analysis system can be transported to other stratigraphic exploratory wells for use as soon as possible after completion of drilling of a well.

It is desired to provide a system and method to effectively analyze in a preliminary way sections of core at the drilling site as the sections of core are being produced. It is further desired to provide such core evaluation without repeated handling of the core for repeated analyses, even where the rate of one analysis step differs from that of one or more of the other analysis steps. It is further desired to provide such core evaluation using a system which is flexible, modular, lightweight, and characterized by low power consumption. Such a system can be used in connection with drilling stratigraphic exploration wells even in remote and difficult to access areas at greatly reduced costs compared to what the result using conventional and available techniques.

SUMMARY OF THE INVENTION

According to an aspect of the invention, a system is provided for analysis of core taken during subterranean stratigraphic exploration.

The system for analyzing core taken during subterranean stratigraphic exploration comprises a core trough comprising a receptacle for receiving a section of core and an engaging portion for directly engaging drive means. Drive means directly engages the engaging portion of the core trough and imparts linear motion to the core trough, driving the core trough adjacent analysis means for analyzing core supported in the core trough, and then self-disengages from the core trough following such movement.

According to another aspect of the invention, there is provided a system for analyzing sections of core supported in core troughs, each core trough comprising a receptacle portion for receiving a section of core and a drive engaging portion. The system comprises two or more analysis modules in series. Each analysis module comprises drive means for engaging the drive engaging portion of the core trough and for driving a core trough along a path, analysis means adjacent the path for analyzing a section of core supported in a core trough as the drive means drives the core trough along the path, and sensing means for generating a signal representative of position of a core trough along the path. There is also provided means for conveying a core trough from engagement with drive means of one module to engagement with drive means of another module and control means for controlling drive means of the two or more modules in series responsive to signals of the sensing means of the two or more modules in series.

DETAILED DESCRIPTION OF THE INVENTION

Figure 1:
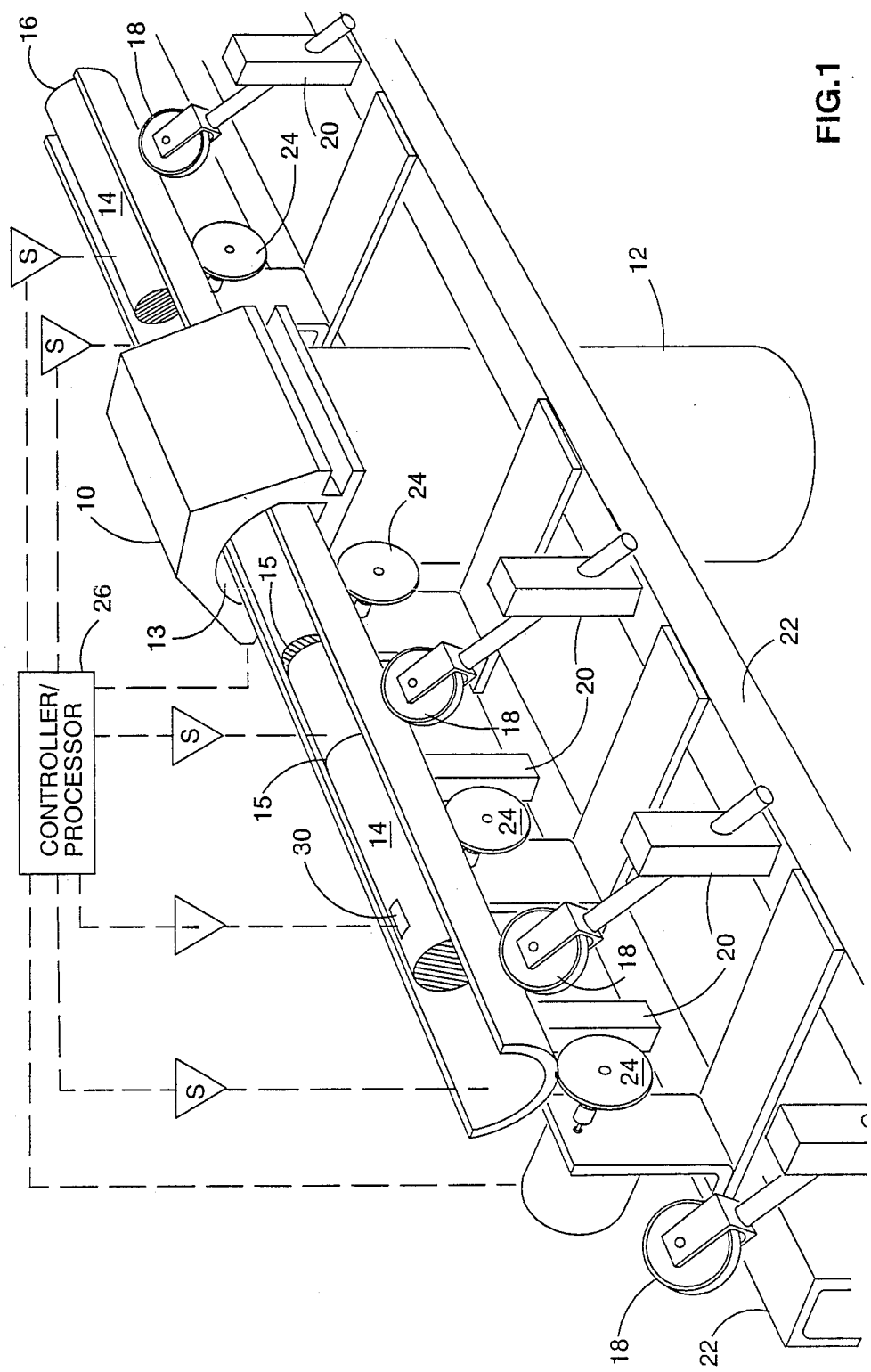
FIG. 1 illustrates in perspective view a module in accordance with the invention for gamma ray analysis of sections of core.

The invention comprises a system for analyzing core taken during subterranean stratigraphic exploration. Subterranean stratigraphic exploration comprises taking large quantities of core during a drilling and coring operation which are then analyzed to determine whether other wells might be drilled for further exploration or for production of oil and gas. By carrying out subterranean stratigraphic exploration, direct information on subterranean stratigraphy is provided which can be used in conjunction with other information resulting from seismic exploration, logging of the stratigraphic exploration well, and the like. In fact, it is expected that subterranean stratigraphic exploration will substantially reduce the extent of seismic and logging data collection.

The system for analyzing cores comprises a core trough which has a receptacle portion for receiving a section of core and which has a drive engaging portion for being directly engaged by drive means which will drive the core trough along a path adjacent analysis means. The core trough is preferably shallow and is preferably open above for for receiving a section of core, which frequently is separated by breaks occurring during handling into several parts. The core trough is typically long and narrow. Preferably, the core trough has a length to width ratio of at least 2:1, preferably 5:1 or even 10:1 or more. The trough has a definite length selected for convenience of handling of the cores and troughs. Lengths of 1 to 6 ft are particularly convenient for handling by one person. The core trough can be constructed of plastics, fiberglass, or other nonmagnetic, preferably nonmetallic material.

In a preferred embodiment, the core trough can be a shallow receptacle which provides sufficient lateral support of the core to prevent rotation of the core during movement through an analysis zone. The core trough can be, for example, U-shaped, V-shaped, and the like. Preferably, the core trough is U-shaped and has an inside diameter somewhat larger than the outside diameter of the sections of core being conveyed thereby. Such core troughs function to support sections of core during analysis. Broken sections of core can be placed in such troughs in their original orientation relative to one another. Since the section is supported against rotation by the trough during analysis, the results of analysis are representative of the orientation of the core prior to breakage.

The drive engaging portion of the core trough can be any suitable mechanical arrangement for directly engaging and being engaged by a drive means and for being self-disengaging when the drive means has completed driving the core conveyor trough through the analysis zone. The engaging portion can be a groove along the underside of the core trough, which receives and is engaged by drive means for imparting linear motion to the core trough. Many mechanical arrangements for drive engaging portions and drive means will be apparent to those skilled in the art. For example, the engaging portion of the trough can be the sides of the trough, and the drive means can have means for engaging the sides. The engaging portion of the core trough can be a portion of the core trough itself, and the drive means can be shaped so as to receive that portion of the core trough, for example, the drive means can comprise a wheel or gear having a concave surface which receives and engages the convex lower surface of the core trough. The drive engaging portion can be toothed and can mesh with toothed gears of the driving means or, alternatively, can be smooth and engaged by friction gears of the driving means. In all cases, in accordance with the invention, the engaging means and the drive means cooperate so that when a core trough engages a drive means, the drive means can impart linear motion to the core trough and so that the core trough and the drive means are self-disengaging when the drive means has driven the core trough a distance about equal to the length of the engaging portion of the core trough.

Each module in accordance with the invention also comprises analysis means adapted for analyzing lengths of core supported in a core trough path adjacent thereto. The analysis means can be any suitable analysis means for preliminary or detailed analysis of core. For example, the core analysis means can be means for gamma ray analysis, infrared analysis, magnetic susceptibility analysis, and the like.

Each module can comprise two or more analyzers. For example, a module can have an infrared analyzer and a magnetic susceptibility analyzer at spaced apart positions along the path of a module. Each analyzer provides signals representative of analyses of sections of core to a controller/processor where the data are correlated with an identifier for the section of core being analyzed and maintained as a record for that section of core.

The invention also comprises drive means for directly engaging the engaging portion of the core trough and for imparting linear motion to the core trough, for driving the core trough along a path adjacent the analysis means for analysis of core supported therein, and for self-disengaging from the core trough following such motion.

Preferably, the drive means is beltless and effective for driving the core trough along the path adjacent the analysis means without the drive means itself traveling along the path adjacent the analysis means together with the trough. Such drive means can be provided by motors driving shafts which can directly engage the engaging portions of a core trough, shafts driving friction rollers or friction gears which directly engage the engaging portion of the core trough, and the like.

Since only the core trough and a section of core passes adjacent the analysis means, the analysis means can be smaller than otherwise possible, can scan the length of core from below, can have a path therethrough which is shaped substantially like the core, and many other advantages. Different advantages become important for different types of analysis. For example, magnetic susceptibility is typically measured using a coil which is easily constructed and interpreted where the coil has a circular shape, such as is possible using the core trough and drive means of the present invention. Magnetic susceptibility coils adapted for passing belted conveyors therethrough are conversely more difficult to construct and interpret. Similarly, it is advantageous and convenient to position a gamma ray analyzer below the core trough, and an infrared analyzer above the core trough, and the like. Apparatus using the core trough and drive means in accordance with the invention can easily accommodate all of these desirable features.

Path means is provided for supporting and guiding core troughs as the core troughs are driven by drive means along the path adjacent analysis means. The path means can comprise a series of rollers, rails, or the like, which support and guide the core troughs during movement. The drive means and the path means can be mounted together on a common frame to provide the necessary cooperation. The path means can extend through the analysis zone or can terminate adjacent a first side of an analysis zone and begin again adjacent the second side of an analysis zone.

The drive means of a module is positioned adjacent the path for driving a core trough along the path. The drive means can include two or more drivers at spaced apart locations along the path. In this way, the length of the core trough can be reduced since the core trough must have a drive engaging portion effective for simultaneously engaging at least two of these spaced apart drive means. Two, three, four, or more drivers can be provided for each module in accordance with the invention. Motors capable of precisely controlled forward and reverse motion are preferred, such as stepper motors.

Sensing means can be provided adjacent the path for position sensing of a core trough along a path. Sensing means can comprise one, two, three, four, or more sensors at spaced apart locations along a path in a module. Each sensor can provide a signal representative of the presence or absence of a core trough adjacent to the position of the sensor. The signals can be provided to a controller, as described below. The sensor means can be, for example, photoelectric cells, microswitches mechanically actuated by passage of the core trough, and the like, suitable for indicating presence of a core trough at a location preferably adjacent the entrance to and/or exit from each analysis zone of a module. In this way, the position of a core trough at positions along the path of a module where control is important can be detected.

The sensing means provides one or more signals representative of position of a core trough to a controller for controlling drive means responsive to the signals. The controller can be, for example, a microprocessor, a computer, or the like, which receives the signals and then responds to the signals under direct operator control or under computer program control by controlling the drive means of a module.

The controller means for different modules can be a sinle computer or microprocessor for a series of modules or each module can have its own controller. In each case, provision is made for the controller of a module being responsive not only to positions of core troughs in that module, but also in adjacent modules.

Identifier recognition means can also be provided adjacent the path means for each module for responding to an identifier, such as a bar code, or the like, placed adjacent each section of core. The identifier provides a signal representative of the section of core being analyzed in a module to the controller. The controller uses the identifier to identify the source of data being taken by the analyzer(s) at that module with the particular section of core being analyzed.

Referring now to the drawings in detail, FIG. 1 illustrates in perspective view a module in accordance with the invention for gamma ray analysis of core.

The gamma ray analysis equipment is housed in housing 12 which shields the instrument from sources of radiation in the environment so that the instrument responds predominantly to the natural radiation of the length of core 14 being assayed. The shield 12 of the gamma ray detector has an opening 13 therein through which the length of core 14 supported by the core trough 16 is passed. A path is defined for passing the core trough through the analysis zone by rollers 18, roller supports 20, and frames 22. A plurality of drive means 24 are provided, for example, stepper motors at spaced apart locations along the path for driving the trough along the path. Each drive means is controlled by controller/processor 26 which receives position signals representative of core trough positions by a plurality of spaced apart sensors S. An identifier sensor I also provides a signal to the controlled process by responding for example to a bar code or other identifier 30 placed on the section of core by the handler.

During operation of the module of FIG. 1, the controller/processor 26 can cause motors 24 to effect movement of a trough containing a core, for example, until the core has passed a short distance, for example, 3 in. past the window of the gamma ray detector. The gamma ray detector scintillation counter is permitted to reset and then controller 26 causes drivers 24 to move the core trough through the analysis zone at a set rate. The gamma ray analyzer can sum counts representative of natural radiation of the core over set lengths of core, for example, every 6 in., and can provide these sums to the controller/processor 26. In the controller/processor 26, the identifier of the core, for example, a bar code sensed by bar code reader I, is associated with the data from the core in such a way as to provide a record of the data matched to a a specific section of core.

Figure 2:
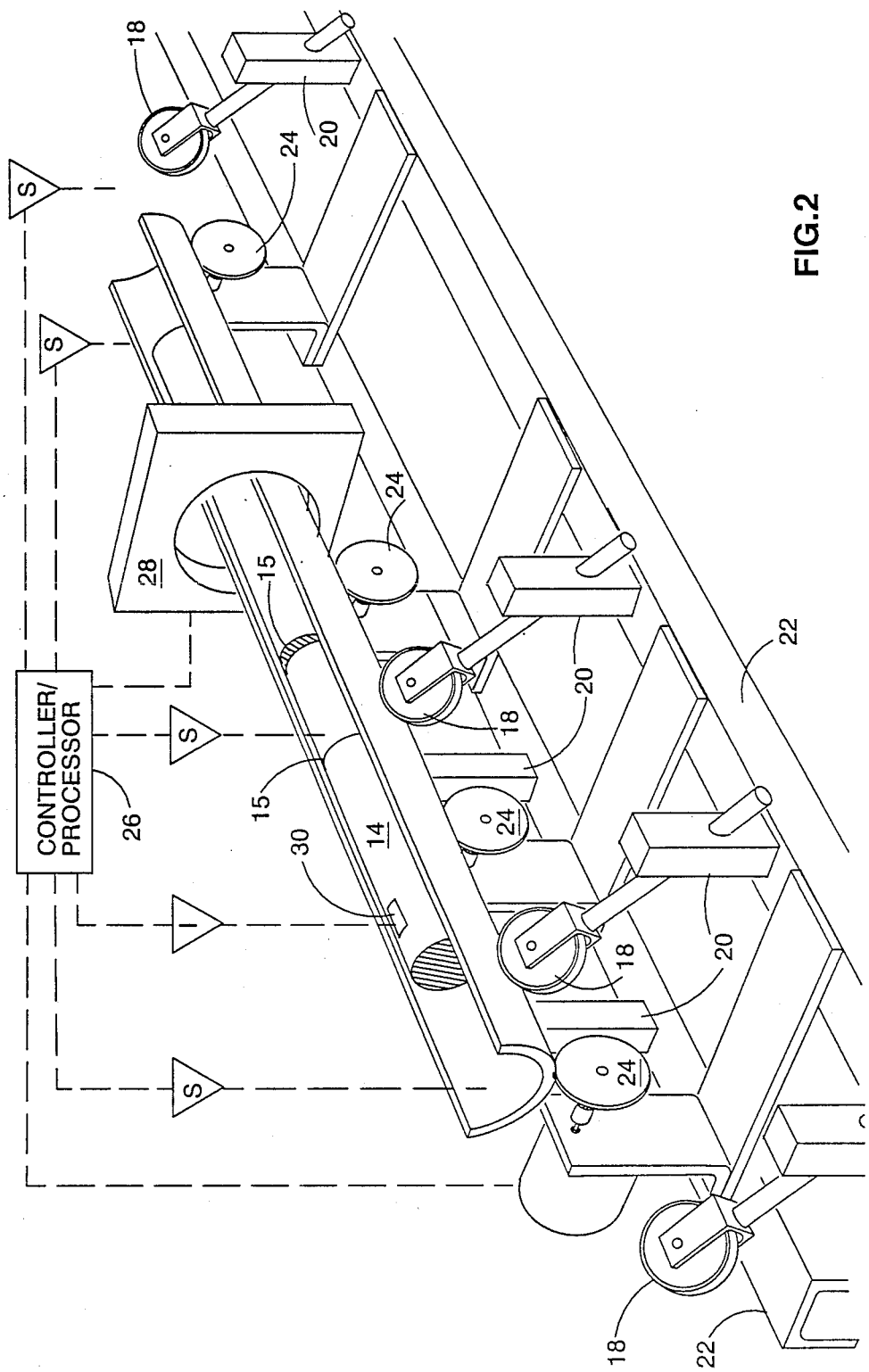
FIG. 2 illustrates in perspective view a module in accordance with the invention for magnetic susceptibility analysis of sections of core.

Referring now to FIG. 2, FIG. 2 illustrates in perspective view a module in accordance with the invention for magnetic susceptibility analysis of the core. The reference numerals in FIG. 2 and the other figures where appropriate are the same as those in FIG. 1. In FIG. 2, a magnetic susceptibility coil is provided at 28. It will be apparent that two or more of the analysis means can be combined into a single module. For example, the gamma ray detector and the magnetic susceptibility detector can be placed adjacent one another in a single analysis module. In this event, following operation of the gamma ray detector for a core, it may be that the core has already passed through the magnetic susceptibility detector to a greater or lesser extent. In this event, the controller/processor can reverse the signals to drive motors 24 returning the core to an appropriate position for beginning the magnetic susceptibility analysis. After zeroing of the magnetic susceptibility detector without any sample in the coil, magnetic susceptibility data can then be taken and provided to controller/processor 26 and correlated or matched with the identifier sensed by identification sensor I.

Figure 3:
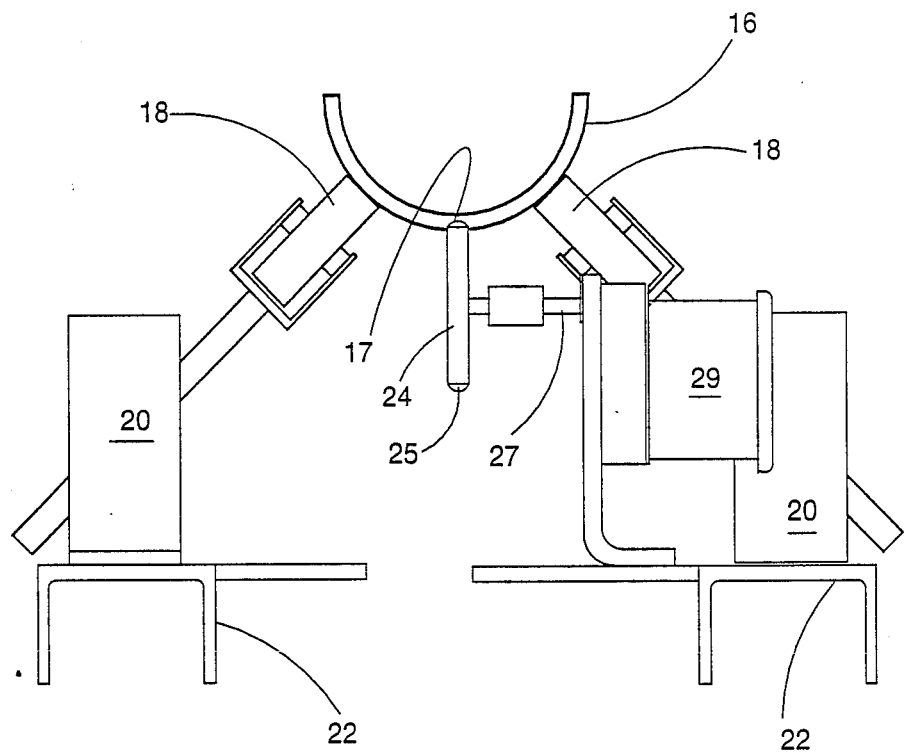
FIG. 3 illustrates in plan view a core trough, its engaging portion, and drive means directly engaging the engaging portion, all in accordance with the invention.

Referring now to FIG. 3, FIG. 3 shows in plan view one embodiment of a core conveyor and drive means in accordance with the invention. As illustrated, the core trough is generally U-shaped and has a drive engaging portion 17 which is a shallow groove in the base of the core trough. Drive means 24 having friction means 25, for example, rubber, or the like is received by drive engaging portion 17 of core trough 16 and is driven by shaft 27 from stepper motor 29. The stepper motor 29 is capable of either forward or reverse rotation so that the core trough can be precisely positioned. Path means 18 and support means 20 and 22 are also shown in the plan view.

Figure 4:
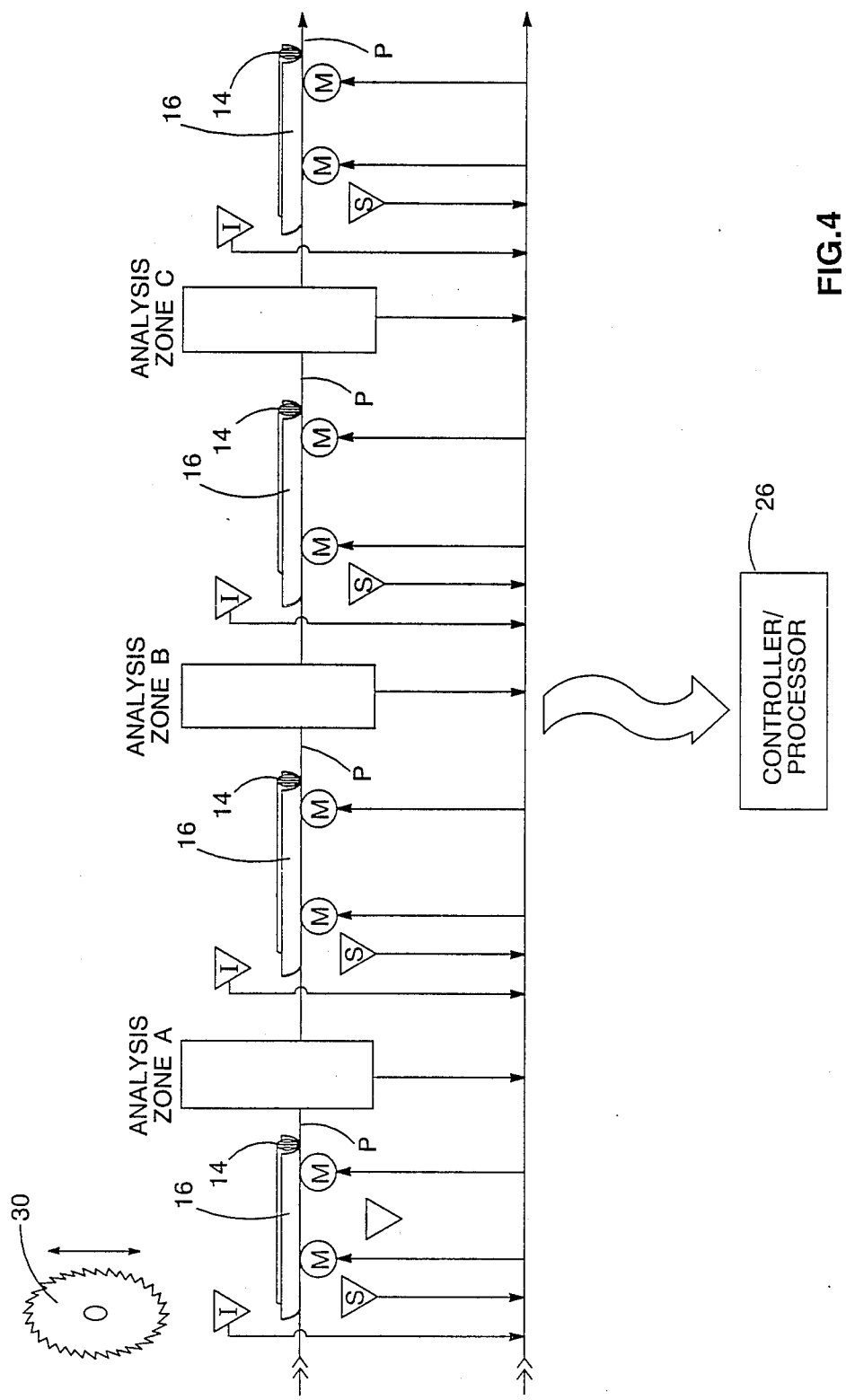
FIG. 4 illustrates schematically a first embodiment of the invention comprising three modular analysis zones in series in accordance with the invention.

Referring now to FIG. 4, FIG. 4 illustrates schematically a first embodiment of the invention comprising three modular analysis zones in accordance with the invention. Thus, FIG. 4 shows the three analysis zones A, B, and C adjacent a path P having motors M, sensors S, and identifiers I associated therewith. A saw 30 is provided for sectioning the cores, typically taken in lengths too long for convenient handling into smaller sections. FIG. 4 illustrates that the controller/processor 26 for a series of analysis zones A, B, and C can be a single controller/processor which controls motors M for all of the modules A, B, C, responsive to sensors S from all of the modules.

Figure 5:
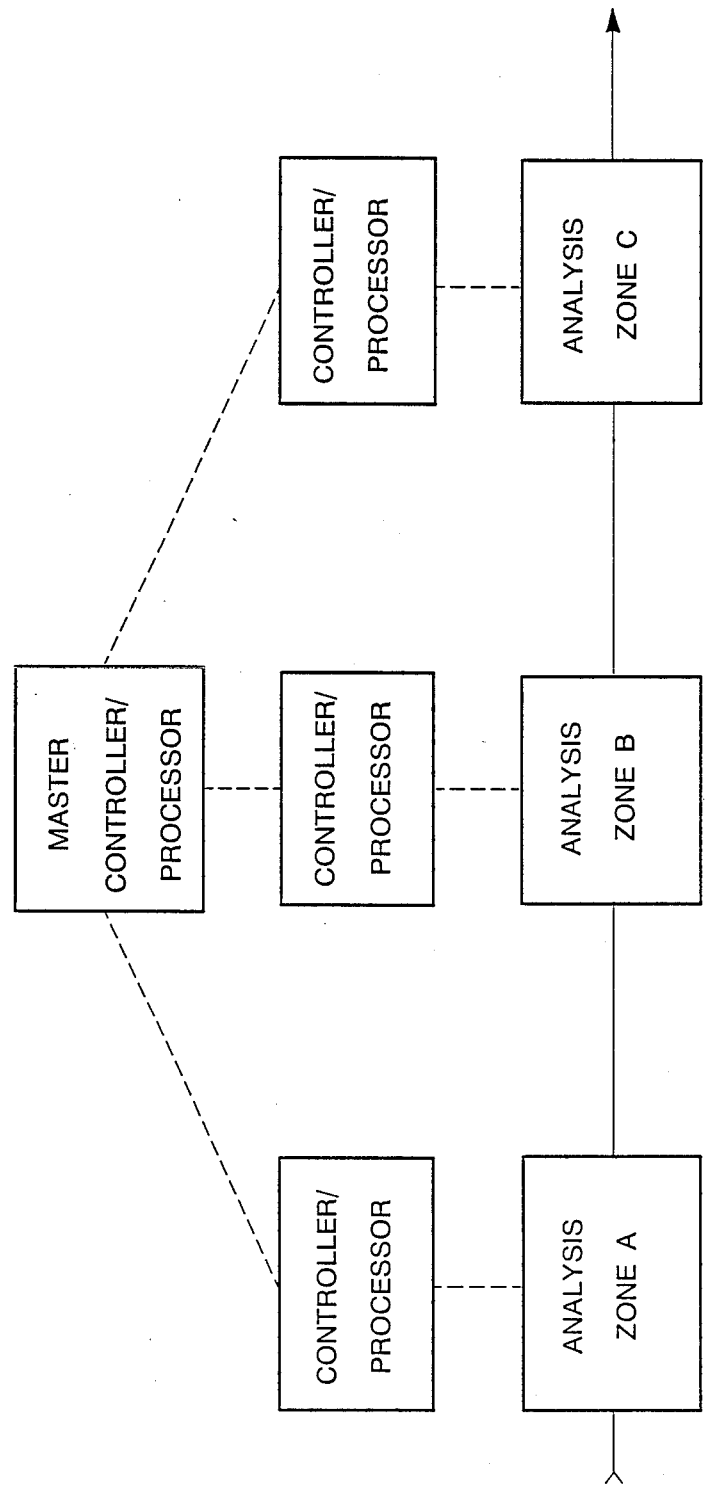
FIG. 5 illustrates schematically a second embodiment of a system comprising three modular analysis zones in series in accordance with the invention.

Referring now to FIG. 5, FIG. 5 illustrates schematically a second embodiment of a system comprising three modular analysis zones A, B, C, in accordance with the invention. In accordance with the embodiment of FIG. 5, each analysis module can be controlled by its own controller/processor, and all of the controller/processors of a system can be controlled by a master controller/processor.

In accordance with either of FIG. 4 or FIG. 5, the controller/processor can control movement of a core trough through one analysis zone, for example, A, responsive to a signal from another analysis zone, for example, B, indicating that such other analysis zone is able to receive a core trough.

Each analysis module receives the core sections in the core troughs from the preceding module, initiates the physical measurements determined by analysis in each module, moves the core trough as required for the measurements, acquires the measurement data from he instruments, passes the core trough to the next module, and sends data to the controller processor.

What is claimed is:

1. A beltless system for conveying and analyzing sections of core comprising:

a core trough comprising a receptacle portion for receiving a section of core and a drive engaging portion for engaging and being engaged by at least two spaced apart drivers and for being self-disengaging from a driver when the driver has driven the core trough a distance about equal to length of the drive engaging portion of the core trough;

drive means comprising at least two spaced apart drivers each having means for engaging the drive engaging portion of the core trough and for imparting linear motion to the core trough and for driving the core trough along a path adjacent an analysis means for analysis of core supported therein and for being self-disengaging from the core trough after driving the core through a distance about equal to length of the driver engaging portion of the core trough;

analysis means adjacent the path for analyzing a section of core supported in the core trough as the drive means drives the core trough along the path.

2. The system of claim 1 wherein each driver of the drive means is effective for driving the core trough along the path adjacent the analysis means without itself traveling along the path adjacent the analysis means together with the core trough.

3. The system of claim 1 wherein each driver of the drive means comprises a motor for imparting rotary motion to a wheel mechanically coupled to a shaft; and wherein the wheel engages the drive engaging portion of the core trough.

4. The system of claim 2 wherein each driver of the drive means comprises a motor for imparting rotary motion to a shaft, and wherein the shaft engages the drive engaging portion of the core trough.

5. The system of claim 1 wherein the analysis means comprises an entrance side and an exit side, wherein the drive means comprises a first driver mounted adjacent the entrance side and second driver mounted adjacent the exit side of the analysis means, wherein the engaging portion of the core trough has a length effective for engaging both the first driver means and the second driver means, and wherein only the core trough and core supported therein passes adjacent the analysis means.

6. The system of claim 1 wherein the drive means comprises a plurality of spaced apart drivers along the path.

7. The system of claim 1 further comprising:

sensing means for sensing position of a core trough along the path.

8. The system of claim 1 further comprising:

sensing means for sensing a core trough along the path, the sensing means comprising a plurality of spaced-part sensors for sensing a core trough at spaced apart positions along the path, and for producing signals representative of position of a core trough along the path.

9. The system of claim 1 further comprising:

sensing means for sensing a core trough along the path, the sensing means comprising a plurality of spaced apart sensors for sensing a core trough at spaced apart positions along the path and for producing signals representative of position of position of a core trough along the path; and control means for controlling drive means responsive to the signals.

10. The system of claim 1 further comprising:

identifier means adjacent the path for responding to an identification on the core identifying the sections of core being carried by a core trough.

11. The system of claim 1 wherein the analysis means comprises at least one means selected from means for magnetic susceptibility analysis, means for gamma ray analysis, and means for infrared analysis, of core.

12. The system of claim 1 wherein the analysis means has a path therethrough shaped substantially like the core.

13. A beltless system for conveying and analyzing a section of core supported in a core trough comprising a receptacle portion for receiving a section of core and a drive engaging portion for engaging and being engaged by at least two spaced apart drivers and for being self-disengaging from a driver when the driver has driven a core trough a distance about equal to length of the drive engaging portion of the core trough, the system comprising:

two or more analysis modules in series, each analysis module comprising:

drive means comprising a driver for engaging the drive engaging portion of the core trough and for imparting linear motion to the core trough for driving the core trough along a path adjacent an analysis means for analysis of core supported therein and for self-disengaging from the core trough after driving the core trough a distance about equal to length of the driver engaging portion of the core trough;

analysis means adjacent the path for analyzing a section of core supported in a core trough as the drive means drives the core trough along the path;

sensing means for generating a signals representative of position of a core trough along the path;

path means for conveying a core trough from engagement with drive means of one module to engagement with drive means of another module; and control means for controlling drive means of the two or more modules in series responsive to the signals of the sensing means of the two or more modules in series.

14. The system of claim 13 wherein each analysis module further comprises:

controller means for controlling the drive means of such module responsive to the signals of the sensing means of the analysis module;

wherein the controller means further controls the drive means of an analysis module responsive to the signals of the sensing means of another analysis module.

15. The system of claim 13
wherein each driver of the drive means is effective for driving the core trough along the path adjacent the analysis means without itself traveling along the path adjacent the analysis means together with the core trough.

16. The system of claim 13
wherein each driver of the drive means of each analysis module comprises a motor for imparting rotary motion to a wheel mechanically coupled to a shaft; and wherein the wheel engages the drive engaging portion of the core trough.

17. The system of claim 13
wherein each driver of the drive means comprises a motor for imparting rotary motion to a shaft, and wherein the shaft engages the drive engaging portion of the core trough.

18. The system of claim 13
wherein the analysis means of each analysis module comprises an entrance side and an exit side, wherein the drive means comprises a first driver mounted adjacent the entrance side and a second driver mounted adjacent the exit side of the analysis means, and wherein the engaging portion of the core trough has a length effective for engaging both the first driver and the second driver; and wherein only the core trough and core supported therein passes adjacent the analysis means.

19. The system of claim 13
wherein the drive means comprises a plurality of spaced apart drivers along the path.

20. The system of claim 13
wherein the sensing means of each analysis module comprises a plurality of spaced-apart sensors for sensing a core trough at spaced apart positions along the path, and for producing signals representative of position of a core trough along the path.

21. The system of claim 13 further comprising:
identifier means adjacent the path for responding to an identification representative of the sections of core being analyzed; and wherein control means associates the identification with analysis data for each section of core.

22. The system of claim 13
wherein the analysis means comprises at least one means selected from means for magnetic susceptibility analysis, means for gamma ray analysis, and means for infrared analysis, of core.

23. The system of claim 13
wherein the analysis means has a path therethrough shaped substantially like the core.

* * * * *